US010232147B2

(12) United States Patent
Liu et al.

(10) Patent No.: US 10,232,147 B2
(45) Date of Patent: Mar. 19, 2019

(54) METHOD FOR ASSEMBLING A SCAFFOLD-BALLOON CATHETER

(71) Applicant: Abbott Cardiovascular Systems Inc., Santa Clara, CA (US)

(72) Inventors: Annie P. Liu, Cupertino, CA (US); Jason Phillips, Lake Elsinore, CA (US); Mark C. Johnson, Murrieta, CA (US); Sean Mcniven, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 434 days.

(21) Appl. No.: 14/834,345

(22) Filed: Aug. 24, 2015

(65) Prior Publication Data

US 2015/0360006 A1  Dec. 17, 2015

Related U.S. Application Data

(60) Division of application No. 13/848,683, filed on Mar. 21, 2013, now Pat. No. 9,119,741, which is a
(Continued)

(51) Int. Cl.
*A61M 25/10* (2013.01)
*A61F 2/00* (2006.01)
(Continued)

(52) U.S. Cl.
CPC .......... *A61M 25/10* (2013.01); *A61F 2/0095* (2013.01); *A61F 2/958* (2013.01); *A61F 2/962* (2013.01);
(Continued)

(58) Field of Classification Search
CPC .............. A61M 25/10; A61M 25/1034; A61M 25/1036; A61M 2025/1081; A61F 2/958;
(Continued)

(56) References Cited

U.S. PATENT DOCUMENTS 4,243,050 A   1/1981  Littleford
4,581,025 A   4/1986  Sheath
(Continued)

FOREIGN PATENT DOCUMENTS

CN   201379671 Y   1/2010
JP   2013-188252   9/2013
(Continued)

OTHER PUBLICATIONS

International Search Report for PCT/US2012/039719, dated Aug. 29, 2012, 13 pgs.
(Continued)

*Primary Examiner* — Jermie Cozart
(74) *Attorney, Agent, or Firm* — Squire Patton Boggs (US) LLP

(57) ABSTRACT

A medical device includes a polymer scaffold crimped to a catheter having an expansion balloon. A sheath pair is placed over the crimped scaffold after crimping to reduce recoil of the crimped polymer scaffold and maintain scaffold-balloon engagement relied on to hold the scaffold to the balloon when the scaffold is being delivered to a target in a body. The sheath pair is removed by a health professional before placing the scaffold within the body.

9 Claims, 6 Drawing Sheets

Related U.S. Application Data continuation of application No. 13/118,311, filed on May 27, 2011, now Pat. No. 8,414,528.

(51) Int. Cl.
  *A61F 2/958* (2013.01)
  *A61F 2/962* (2013.01)
  *A61F 2/95* (2013.01)

(52) U.S. Cl.
  CPC . *A61M 25/1036* (2013.01); *A61F 2002/9522* (2013.01); *A61M 2025/1081* (2013.01); *Y10T 29/49865* (2015.01); *Y10T 29/49913* (2015.01)

(58) Field of Classification Search
  CPC .... A61F 2/962; A61F 2/97; A61F 2002/9665; Y10T 29/49865; Y10T 29/49913; Y10T 29/49927; Y10T 29/49929
  See application file for complete search history.

(56) References Cited

U.S. PATENT DOCUMENTS

| | | | |
|---|---|---|---|
| 4,710,181 A | 12/1987 | Fuqua | |
| 4,846,811 A | 7/1989 | Vanderhoof | |
| 5,015,231 A | 5/1991 | Keith et al. | |
| 5,158,545 A | 10/1992 | Trudell et al. | |
| 5,211,654 A | 5/1993 | Kaltenbach | |
| 5,250,033 A | 10/1993 | Evans et al. | |
| 5,352,236 A | 10/1994 | Jung et al. | |
| 5,386,817 A | 2/1995 | Jones | |
| 5,458,615 A | 10/1995 | Klemm et al. | |
| 5,545,211 A | 8/1996 | An et al. | |
| 5,569,294 A | 10/1996 | Parkola | |
| 5,591,226 A | 1/1997 | Trerotola et al. | |
| 5,643,175 A | 7/1997 | Adair | |
| 5,647,857 A | 7/1997 | Anderson et al. | |
| 5,653,697 A | 8/1997 | Quiachon et al. | |
| 5,693,066 A | 12/1997 | Rupp et al. | |
| 5,709,703 A | 1/1998 | Lukic et al. | |
| 5,749,852 A | 5/1998 | Schwab et al. | |
| 5,765,682 A | 6/1998 | Bley et al. | |
| 5,776,141 A | 7/1998 | Klein et al. | |
| 5,782,855 A | 7/1998 | Lau et al. | |
| 5,800,517 A | 9/1998 | Anderson et al. | |
| 5,817,100 A | 10/1998 | Igaki | |
| 5,868,707 A | 2/1999 | Williams et al. | |
| 5,893,868 A | 4/1999 | Holman et al. | |
| 5,964,730 A | 10/1999 | Williams et al. | |
| 5,992,000 A | 11/1999 | Humphrey et al. | |
| 6,010,529 A | 1/2000 | Herweck et al. | |
| 6,013,854 A | 1/2000 | Moriuchi | |
| 6,110,146 A | 8/2000 | Berthiaume et al. | |
| 6,132,450 A | 10/2000 | Hanson et al. | |
| 6,152,944 A | 11/2000 | Holman et al. | |
| 6,197,016 B1 | 3/2001 | Fourkas et al. | |
| 6,254,609 B1 | 7/2001 | Vrba et al. | |
| 6,334,867 B1 | 1/2002 | Anson | |
| 6,342,066 B1 | 1/2002 | Toro et al. | |
| 6,355,013 B1 | 3/2002 | Van Muiden | |
| 6,416,529 B1 | 7/2002 | Holman et al. | |
| 6,533,806 B1 | 3/2003 | Sullivan et al. | |
| 6,749,584 B2 | 6/2004 | Briggs et al. | |
| 6,783,542 B2 | 8/2004 | Eidenschink | |
| 6,790,224 B2 | 9/2004 | Gerberding | |
| 6,805,703 B2 | 10/2004 | McMorrow | |
| 6,827,731 B2 | 12/2004 | Armstrong et al. | |
| 6,899,727 B2 | 5/2005 | Armstrong et al. | |
| 7,172,620 B2 | 2/2007 | Gilson | |
| 7,198,636 B2 | 4/2007 | Cully et al. | |
| 7,300,456 B2 | 11/2007 | Andreas | |
| 7,314,481 B2 | 1/2008 | Karpiel | |
| 7,347,868 B2 | 3/2008 | Burnett et al. | |
| 7,384,426 B2 | 6/2008 | Wallace et al. | |
| 7,618,398 B2 | 11/2009 | Holman et al. | |
| 7,918,880 B2 | 4/2011 | Austin | |
| 8,046,897 B2 | 11/2011 | Wang et al. | |
| 8,052,912 B2 | 11/2011 | Gale et al. | |
| 8,308,789 B2 | 11/2012 | Armstrong | |
| 8,414,528 B2 | 4/2013 | Liu et al. | |
| 8,539,663 B2 | 9/2013 | Wang et al. | |
| 8,752,261 B2 | 6/2014 | Van Sciver | |
| 8,852,257 B2 | 10/2014 | Liu et al. | |
| 9,072,590 B2 | 7/2015 | Wang et al. | |
| 9,119,741 B2 | 9/2015 | Liu et al. | |
| RE45,744 E | 10/2015 | Gale et al. | |
| 9,364,361 B2 | 6/2016 | Duong et al. | |
| 9,572,699 B2 | 2/2017 | Liu et al. | |
| 9,579,181 B2 | 2/2017 | Wang et al. | |
| 9,675,483 B2 | 6/2017 | Pacetti et al. | |
| 9,788,983 B2 | 10/2017 | Johnson et al. | |
| 9,913,958 B2 | 3/2018 | Ciurea et al. | |
| 2001/0001128 A1 | 5/2001 | Holman et al. | |
| 2001/0004735 A1 | 6/2001 | Kindo et al. | |
| 2002/0052640 A1 | 5/2002 | Bigus et al. | |
| 2002/0099431 A1 | 7/2002 | Armstrong et al. | |
| 2003/0004561 A1 | 1/2003 | Bigus et al. | |
| 2003/0055481 A1 | 3/2003 | McMorrow | |
| 2003/0212373 A1 | 11/2003 | Hall et al. | |
| 2004/0073286 A1 | 4/2004 | Armstrong et al. | |
| 2004/0093005 A1 | 5/2004 | Durcan | |
| 2004/0098118 A1 | 5/2004 | Granada et al. | |
| 2004/0133261 A1 | 7/2004 | Bigus et al. | |
| 2004/0143315 A1 | 7/2004 | Bruun et al. | |
| 2005/0288764 A1 | 12/2005 | Snow et al. | |
| 2006/0015135 A1 | 1/2006 | Vrba et al. | |
| 2006/0015171 A1 | 1/2006 | Armstrong et al. | |
| 2006/0036310 A1 | 2/2006 | Spencer et al. | |
| 2007/0061001 A1 | 3/2007 | Durcan et al. | |
| 2007/0208408 A1 | 9/2007 | Weber et al. | |
| 2007/0289117 A1 | 12/2007 | Huang et al. | |
| 2008/0010947 A1 | 1/2008 | Huang et al. | |
| 2008/0016668 A1 | 1/2008 | Huang et al. | |
| 2008/0319388 A1 | 12/2008 | Slattery et al. | |
| 2009/0221965 A1 | 9/2009 | Osypka | |
| 2009/0254169 A1 | 10/2009 | Spenser et al. | |
| 2010/0004735 A1 | 1/2010 | Yang et al. | |
| 2010/0063571 A1 | 3/2010 | Roach et al. | |
| 2011/0184509 A1 | 7/2011 | Von Oepen et al. | |
| 2011/0208292 A1 | 8/2011 | Von Oepen et al. | |
| 2012/0042501 A1 | 2/2012 | Wang et al. | |
| 2012/0109281 A1 | 5/2012 | Papp | |
| 2012/0261858 A1 | 10/2012 | Roberts et al. | |
| 2012/0285609 A1 | 11/2012 | Wang | |
| 2015/0088240 A1 | 3/2015 | Lam et al. | |
| 2015/0360006 A1 | 12/2015 | Liu et al. | |
| 2016/0317337 A1 | 11/2016 | Duong et al. | |
| 2016/0317338 A1 | 11/2016 | Duong et al. | |
| 2017/0151078 A1 | 6/2017 | Speck | |
| 2017/0312110 A1 | 11/2017 | Pacetti et al. | |

FOREIGN PATENT DOCUMENTS

| | | |
|---|---|---|
| WO | WO9622745 A1 | 8/1996 |
| WO | WO9811846 A1 | 3/1998 |
| WO | WO 98/39056 | 9/1998 |
| WO | WO 02/060345 | 8/2002 |
| WO | WO 2011/094048 | 8/2011 |

OTHER PUBLICATIONS

European Search Report, European Application No. EP17159927, Search Report dated Jul. 7, 2017, 3 pages.
Chinese First Office Action, Notice of Reasons for Rejection with English translation for application No. 201610333770.7, dated Apr. 18, 2017.
Japan Patent Office, Notice of Reasons for Rejection with English translation for application No. 2014-512167, dated Mar. 1 , 2016.

METHOD FOR ASSEMBLING A SCAFFOLD-BALLOON CATHETER

CROSS REFERENCE TO RELATED APPLICATION

This application is a divisional of U.S. application Ser. No. 13/848,683, filed Mar. 21, 2013 (U.S. Pat. No. 9,119,741), which is a continuation of U.S. application Ser. No. 13/118,311, filed May 27, 2011 (U.S. Pat. No. 8,414,528), the entire contents of which are hereby incorporated by reference.

FIELD OF THE INVENTION

The present invention relates to drug-eluting medical devices; more particularly, the invention relates to sheaths for polymeric scaffolds crimped to a delivery balloon.

BACKGROUND OF THE INVENTION

A variety of non-surgical interventional procedures have been developed over the years for opening stenosed or occluded blood vessels in a patient caused by the build up of plaque or other substances on the walls of the blood vessel. Such procedures usually involve the percutaneous introduction of an interventional device into the lumen of the artery. In one procedure the stenosis can be treated by placing an expandable interventional device such as an expandable stent into the stenosed region to hold open and sometimes expand the segment of blood vessel or other arterial lumen. Metal or metal alloy stents have been found useful in the treatment or repair of blood vessels after a stenosis has been compressed by percutaneous transluminal coronary angioplasty (PTCA), percutaneous transluminal angioplasty (PTA) or removal by other means. Metal stents are typically delivered in a compressed condition to the target site, then deployed at the target into an expanded condition or deployed state to support the vessel.

The following terminology is used. When reference is made to a "stent", this term will refer to a metal or metal alloy structure, generally speaking, while a scaffold will refer to a polymer structure. It is understood, however, that the art sometimes uses the term "stent" when referring to either a metal or polymer structure.

Metal stents have traditionally fallen into two general categories—balloon expanded and self-expanding. The later type expands to a deployed or expanded state within a vessel when a radial restraint is removed, while the former relies on an externally-applied force to configure it from a crimped or stowed state to the deployed or expanded state.

For example, self-expanding stents formed from, for example, shape memory metals or super-elastic nickel-titanium (NiTi) alloys are designed to automatically expand from a compressed state when the stent is advanced out of a distal end of the delivery catheter into the body lumen, i.e. when the radial restraint is withdrawn or removed. Typically, these stents are delivered within a radially restraining polymer sheath. The sheath maintains the low profile needed to navigate the stent towards the target site. Once at the target site, the sheath is then removed or withdrawn in a controlled manner to facilitate deployment or placement at the desired examples. Examples of self-expanding stents constrained within a sheath when delivered to a target site within a body are found in U.S. Pat. No. 6,254,609, US 20030004561 and US 20020052640.

Balloon expanded stents, as the name implies, are expanded upon application of an external force through inflation of a balloon, upon which the stent is crimped. The expanding balloon applies a radial outward force on the luminal surfaces of the stent. During the expansion from a crimped or stowed, to deployed or expanded state the stent undergoes a plastic or irreversible deformation in the sense that the stent will essentially maintain its deformed, deployed state after balloon pressure is withdrawn.

Balloon expanded stents may also be disposed within a sheath, either during a transluminal delivery to a target site or during the assembly of the stent-balloon catheter delivery system. The balloon expanded stent may be contained within a sheath when delivered to a target site to minimize dislodgment of the stent from the balloon while en route to the target vessel. Sheaths may also be used to protect a drug eluting stent during a crimping process, which presses or crimps the stent to the balloon catheter. When an iris-type crimping mechanism, for example, is used to crimp a stent to balloon, the blades of the crimper, often hardened metal, can form gouges in a drug-polymer coating or even strip off coating such as when the blades and/or stent struts are misaligned during the diameter reduction. Examples of stents that utilize a sheath to protect the stent during a crimping process are found in U.S. Pat. Nos. 6,783,542 and 6,805,703.

A polymer scaffold, such as that described in US 20100004735 may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away after the scaffold has been implanted at the target vessel. The polymer scaffold described in US 2010/0004735, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it is believed that biodegradable scaffolds, as opposed to a metal stent, allow for improved healing of the anatomical lumen and reduced incidence of late stent thrombosis. In these cases, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a delivery system having a polymer scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bioabsorbable polymer such as PLLA or PLGA. Challenges faced when securing a polymer scaffold to a delivery balloon are discussed in U.S. patent application Ser. No. 12/861,719.

When using a polymer scaffold, several of the accepted processes for metal stent handling can no longer be used. A metal stent may be crimped to a balloon in such a manner as to minimize, if not eliminate recoil in the metal structure after removal from the crimp head. Metal materials used for stents are generally capable of being worked more during the crimping process than polymer materials. This desirable property of the metal allows for less concern over the metal stent—balloon engagement changing over time when the stent-catheter is packaged and awaiting use in a medical procedure. Due to the material's ability to be worked during the crimping process, e.g., successively crimped and released at high temperatures within the crimp mechanism, any propensity for elastic recoil in the material following crimping can be significantly reduced, if not eliminated, without affecting the stent's radial strength when later expanded by the balloon. As such, following a crimping process the stent-catheter assembly often does not need packaging or treatment to maintain the desired stent-balloon engagement and delivery profile. If the stent were to recoil to a larger diameter, meaning elastically expand to a larger diameter after the crimping forces are withdrawn, then significant dislodgment force could be lost and the stent-balloon profile not maintained at the desired diameter needed to deliver the stent to the target site.

While a polymer scaffold may be formed so that it is capable of being crimped in such a manner as to reduce inherent elastic recoil tendencies in the material when crimped, e.g., by maintaining crimping blades on the scaffold surface for an appreciable dwell period, the effectiveness of these methods are limited. Significantly, the material generally is incapable of being worked to the degree that a metal stent may be worked without introducing deployed strength problems, such as excessive cracking in the material. Recoil of the crimped structure, therefore, is a problem that needs to be addressed.

In view of the foregoing, there is a need to address the challenges associated with securing a polymer scaffold to a delivery balloon and maintaining the integrity of a scaffold-balloon catheter delivery system up until the time when the scaffold and balloon are delivered to a target site within a body.

SUMMARY OF THE INVENTION

The invention is directed to sheaths used to maintain a polymer scaffold balloon engagement and delivery system profile and methods for assembly of a medical device including a balloon expandable polymer scaffold contained within a sheath. The invention is also directed to a sheath and methods for applying a sheath that enable the sheath to be easily removed by a medical professional, e.g., a doctor, in an intuitive manner without disrupting the crimped scaffold-balloon engagement or damaging the scaffold. Sheaths according to the invention are removed before the medical device is introduced into a patient.

Sheaths according to the invention are particularly useful for maintaining scaffold-balloon engagement and desired delivery profile following a crimping process for scaffolds formed at diameters near to, or larger than a deployed diameter are crimped down to a crossing-profile, or crimped diameter. A scaffold formed at these diameters can exhibit enhanced radial strength when supporting a vessel, as compared to a scaffold formed nearer to a crimped diameter. A scaffold formed near to a deployed diameter, however, increases the propensity for elastic recoil in the scaffold following the crimping process, due to the shape memory in the material. The shape memory relied on for enhancing radial strength at deployment, therefore, also introduces greater elastic recoil tendencies for the crimped scaffold. Recoil both increases the crossing profile and reduces the scaffold-balloon engagement needed to hold the scaffold on the balloon. In one aspect, the invention is directed to maintaining the crossing profile and/or maintaining balloon-scaffold engagement for scaffolds formed near to a deployed diameter.

In another aspect, the invention is directed to a method of assembly of a catheter that includes crimping a polymer scaffold to a balloon of the catheter and within a short period of removal of the scaffold from the crimper placing a restraining sheath over the scaffold. The steps may further include applying an extended dwell time following a final crimping of the scaffold, followed by applying the restraining sheath. Both the crimping dwell time and applied restraining sheath are intended to reduce recoil in the crimped scaffold. The restraining sheath may include both a protecting sheath and a constraining sheath.

In another aspect, the invention is directed to a sterilized medical device, e.g., by E-beam radiation, contained within a sterile package, the package containing a scaffold crimped to a balloon catheter and a sheath disposed over the crimped scaffold to minimize recoil of the crimped scaffold. The sheath covers the crimped scaffold and extends beyond a distal end of the catheter. The sheath may extend at least the length of the scaffold beyond the distal end of the catheter. At the distal end of the sheath there is an portion configured for being manually grabbed and pulled distally of the catheter to remove the sheath from the catheter.

In another aspect, the invention is directed to an apparatus and methods for removing a sheath pair from a scaffold in a safe, intuitive manner by a health professional. According to this aspect of the invention, the sheath pair may be removed by a medical specialist such as a doctor without risk of the scaffold becoming dislodged from the balloon or damaged, such as when the sheath pair is accidentally removed in an improper manner by a health professional.

Sheaths arranged according to the invention provide an effective radial constraint for preventing recoil in a crimped scaffold, yet are comparatively easy to manually remove from the scaffold. A sheath that applies a radial constraint can be difficult to remove manually without damaging the crimped scaffold, dislodging or shifting it on the balloon. In these cases it is desirable to arrange the sheaths in a manner to apply an effective radial constraint yet make the sheaths capable of manual removal in a safe and intuitive manner. By making the sheath removal process easy to follow and intuitive, the possibility that a health professional will damage the medical device when removing the sheath is reduced.

According to another aspect of the invention a crimped scaffold is constrained within a protecting sheath and a constraining sheath. The protecting sheath protects the integrity of the crimped scaffold-balloon structure while the constraining sheath is applied and/or removed from the crimped scaffold. Arranged in this manner a radial inward force may be applied to a crimped scaffold via a sheath, without risking dislodgement or shifting of the scaffold on the balloon when the sheath is manually removed.

According to another aspect, a sheath pair is used to impose a higher radial inward constraint on a crimped polymer scaffold than is possible using a single sheath that must be manually removed from the scaffold before the scaffold can be introduced into a patient.

According to another aspect of the invention, a sheath pair covering a crimped scaffold is removed by sliding a first sheath over a second sheath until the first sheath abuts an end of the second sheath, at which point the second sheath is removed by simultaneously pulling on both sheaths.

In accordance with the foregoing objectives, in one aspect of the invention there is a method for assembling a scaffold-balloon catheter, comprising providing a balloon-catheter having a scaffold crimped to the balloon; and constraining the crimped scaffold including placing a protecting sheath over the scaffold to protect the scaffold, then pushing a constraining sheath over the protecting sheath to constrain recoil in the scaffold using the constraining sheath; wherein the scaffold is configured for being passed through the body of a patient only after the constraining sheath and protecting sheath are removed.

In another aspect, there is an apparatus, comprising a catheter assembly having a distal end and including a scaffold comprising a polymer crimped to a balloon; a sheath disposed over the scaffold, the sheath applying a radial inward force on the crimped scaffold to limit recoil of the scaffold; the sheath extending distally of the catheter distal end by about a length equal to the length of the scaffold; and wherein the apparatus is configured for being passed through the body of a patient only after the sheath is removed. The sheath may comprise a protecting sheath and a constraining sheath that is placed over the protecting sheath and the crimped scaffold to limit recoil of the scaffold by an applying an inwardly directed radial force on the crimped scaffold.

In another aspect, there is an apparatus, comprising a scaffold crimped to a balloon of a catheter, the catheter having a distal end and the scaffold being crimped to the balloon proximally of the distal end; a first sheath disposed over the scaffold, the first sheath including an extension that is distal of the catheter distal end; and a second sheath disposed over the scaffold; wherein the first sheath and second sheath are configured such that the apparatus is capable of being configured into a medical device suitable for being introduced into a patient by (a) pulling the second sheath distally along the first sheath outer surface such that the second sheath is displaced to a location substantially distal of the scaffold or the catheter distal end, and (b) after the first sheath has been moved to the substantially distal location, removing the first sheath from the scaffold by pulling the second sheath against the first sheath extension, thereby displacing the first sheath distally with the second sheath.

In another aspect, there is an apparatus, comprising a scaffold crimped to a balloon of a catheter, the catheter having a distal end and the scaffold being crimped to the balloon proximally of the distal end; a first sheath disposed over the scaffold, the first sheath including an extension distal of the catheter distal end and a portion forming an interfering ledge disposed proximal to the scaffold; and a second sheath disposed over the scaffold and first sheath, the second sheath applying a preload to the scaffold and the first sheath to maintain contact between the first sheath and scaffold; wherein the first sheath is removable from the scaffold only after the second sheath has been moved to the distal extension such that the interfering ledge is capable of deflecting away from the scaffold only when the second sheath is removed from the scaffold; and wherein the apparatus is configured as a medical device suitable for being introduced into a patient when the first and second sheaths are removed from the catheter.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION OF EMBODIMENTS

A polymer scaffold according to a preferred embodiment is formed from a radially expanded, or biaxially expanded extruded PLLA tube. The scaffold is laser cut from the expanded tube. The diameter of the tube is preferably selected to be about the same, or larger than the intended deployed diameter for the scaffold to provide desirable radial strength characteristics, as explained earlier. The scaffold is then crimped onto the balloon of the balloon catheter. Preferably, an iris-type crimper is used to crimp the scaffold to the balloon. The desired crimped profile for the scaffold is ½ or less than ½ of the starting (pre crimp) diameter of the expanded tube and scaffold. In the embodiments the ratio of the starting diameter (before crimping) to the final crimp diameter may be 2:1, 2.5:1, 3:1, or higher. For example, the ratio of starting diameter to final crimped diameter may be greater than the ratio of the deployed diameter to the final crimped diameter of the scaffold, e.g., from about 4:1 to 6:1.

The pre-crimp memory in the scaffold material following crimping will induce some recoil when the scaffold is removed from the crimper. While a dwell period within the crimper can reduce this recoil tendency, it is found that there is residual recoil that needs to be restrained while the scaffold is awaiting use. This is done by placing a restraining sheath over the scaffold immediately after the crimper blades are released and the scaffold removed from the crimper head. This need to reduce recoil is particularly evident when the diameter reduction during crimping is high, since for a larger starting diameter compared to the crimped diameter the crimped material can have higher recoil tendencies. Examples of polymers that may be used to construct sheaths described herein are Pebax, PTFE, Polyethelene, Polycarbonate, Polymide and Nylon. Examples of restraining sheaths for polymer scaffold, and methods for attaching and removing restraining sheaths for polymer scaffold are described in U.S. application Ser. No. 12/916,349.

Figure 1:
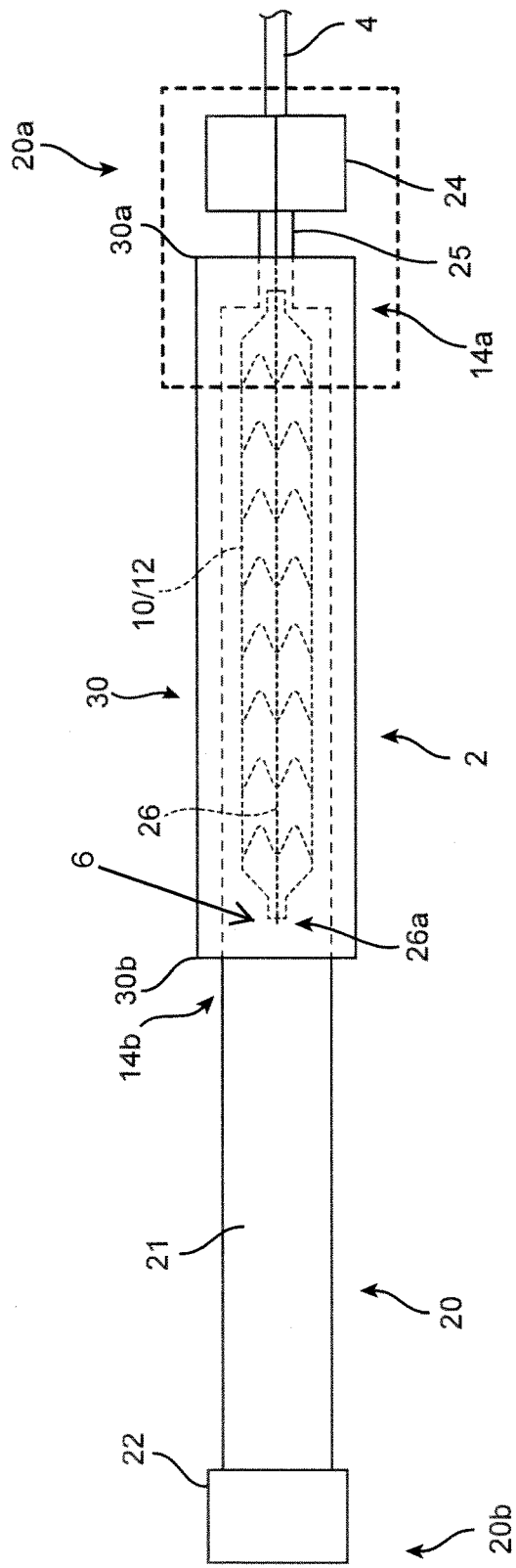
FIG. 1 is a side view of a polymer scaffold-balloon catheter assembly (medical device) with a pair of sheaths placed over the crimped scaffold.

FIG. 1 shows a side view of a distal portion of a scaffold-balloon catheter assembly 2. The catheter assembly 2 includes a catheter shaft 4 and a scaffold 10 crimped to a delivery balloon 12. As shown there are two separate sheaths 20, 30 disposed over the scaffold 10. The scaffold 10 is contained within a protecting sheath 20 and a constraining sheath 30, which is slid over the outer surface of the protecting sheath 20 to position it over the scaffold 10. Before inserting the catheter assembly 2 distal end within a patient, both the constraining sheath 30 and protecting sheath 20 are removed by a health professional.

The sheaths 20, 30 provide an effective radial constraint for reducing recoil in the crimped scaffold 10. Yet the sheaths 20, 30 are also easily removed by a health professional at the time of a medical procedure. A sheath that applies a radial constraint can be difficult to manually remove without adversely affecting the structural integrity of the medical device. In these cases, it is desirable to arrange the sheaths so that special handling is not required by the health professional when the sheath is manually removed. By making the sheath removal process easy to follow or intuitive, the possibility that a health professional will damage the medical device by improperly removing the sheath is reduced.

The constraint imposed by the sheaths 20, 30 maintain the scaffold 10 at essentially the same, or close to the same diameter it had when removed from the crimping mechanism, i.e., the crimped crossing profile, which is needed for traversing tortuous vessels to deliver the scaffold 10 to a target location in a body. The sheath 30 is tightly fit over the sheath 20 and scaffold 10 so that the radial inward force applied on the scaffold 10 can reduce recoil in the scaffold 10. The health professional may then remove both sheaths at the time of the medical procedure. As such, any potential recoil in the scaffold 10 prior to using the medical device is minimized.

The sheath 30, although imposing a tight fit on the scaffold 10 (through sheath 30), can be easily removed by a health professional without risk of the scaffold 10 being accidentally pulled off of the balloon 12. This is accomplished by the manner in which the sheath 20 is positioned and removed from the scaffold 10. If there are excessive pulling forces on the scaffold 10 when sheaths are removed, the scaffold 10 may dislodge from a balloon 12, or shift on the balloon 12, thereby reducing scaffold-balloon engagement relied on to hold the scaffold 10 to the balloon 12.

When the scaffold 10 is constrained by sheath 30, as in FIG. 1, the constraining sheath 30 is located over the section of the protecting sheath 20 where the crimped scaffold 10 is found. This sheath 30 is made from a polymer tube material having a thickness and pre-stressed inner diameter size suitably chosen to cause the sheath 30 to apply a radially inward directed force on the scaffold 10. The thicker the tube and the smaller the pre-stressed inner diameter size for the sheath 30 the higher this constraint will be on the scaffold 10. However, the sheath 30 thickness should not be too thick, nor its inner diameter too small as this will make it difficult to slide the sheath 30 over, or remove the sheath 30 from the scaffold 10. If excessive force is needed to reposition the sheath 30, the scaffold 10 can dislodge from the balloon 12 or become damaged when the sheath 30 is moved.

If only the single sheath 30 were used to constrain the scaffold 10, i.e., the sheath 20 is not present, the amount of preload that the sheath 30 could apply to the scaffold 10 without affecting scaffold-balloon engagement would be limited. However, by introducing the protecting sheath 20 between the scaffold-balloon surface and sheath 30 the sheath 30 can impose a higher preload on the scaffold 10 without risk to the integrity of the scaffold-balloon engagement when the sheath 30 is applied to and/or removed from the scaffold 10. The protecting sheath 20 therefore serves to protect the integrity of the scaffold-balloon structure as the sheath 30 is repositioned relative to the scaffold 10.

The protecting sheath 20 extends over the entire length of the scaffold (as shown) and beyond the distal tip 6 of the catheter, for reasons that will become apparent. The protecting sheath 20 is preferably formed from a unitary piece of polymer material, which is shaped to form differently sized portions 22, 24 and 25 for protecting the scaffold/balloon 10/12.

At the distal end 20b of sheath 20 there is a raised end 22 in the form of a cylinder section having a larger diameter than the body portion 21 of the sheath 20 to the right of end 22 which covers the scaffold 10 in FIG. 1. As such, raised end 22 provides an abutting surface with respect to distal movement of sheath 30, i.e., end 30b of sheath 30 abuts end 22 when sheath 30 is moved to the left in FIG. 1. End 22 may alternatively take the shape of a cone with the largest diameter end of the cone being the most distal end of the sheath 20. The raised end 22 is used to remove the sheaths 20, 30, as explained below.

The protecting sheath 20 has a cut 26, extending from the proximal end 20a to a location about at the distal the tip 6 of the catheter assembly 2. The cut 26 forms an upper and lower separable halve 28, 29 of the sheath 20. These halves 29, 28 are configured to freely move apart when the sheath 30 is positioned towards the distal end 20b. The location 26a may be thought of as a living hinge 26a about which the upper half 29 and lower half 28 of the sheath 20 can rotate, or deflect away from the scaffold 10. When sheath 30 is moved distally of the scaffold 10 in FIG. 1, the halves 28, 29 will tend to open up naturally, due to the preload applied by sheath 30 near hinge 26a (the separable halves 28, 29 can be more clearly seen in FIGS. 2A-2D). This arrangement for halves 29, 28 allows sheath 20 it to be easily removed from the scaffold 10 with minimal disruption to scaffold-balloon structural integrity, after sheath 30 is moved to distal end 20b. When sheath 30 is being fitted over the scaffold 10 or removed from the scaffold 10, the presence of the halves 28, 29 prevent direct contact between the sliding sheath 30 and the surface of the scaffold 10.

At a proximal end 20a of sheath 20 there are portions 24 and 25 formed when the combined proximal ends of halves 28, 29 are brought together as in FIG. 1. When the halves 28, 29 are brought together the portions 24 and 25 take the form of a stepped or notched portion 25 and a raised end 24 similar to end 22, as shown in FIG. 1 and the cross-sectional view of the proximal end 20a of the assembly of FIG. 1A. The notched or stepped portion 25 has an outer diameter less than the outer diameter of the portion 21 of the sheath that covers the scaffold 10, as well as the outer diameter of the scaffold/balloon 10/12. The raised end 24 has a diameter that is greater than the body portion 21. The raised end 24 provides an abutment or stop 24a preventing the proximal end 30a of the sheath 30 from moving to the right in FIG.

1. As such, the end 24 prevents the sheath 30 from sliding off of the scaffold 10. The portion 24 also serves to identify the approximate location of the sheath 30 proximal end 30a so that it is fitted over the scaffold 10 and balloon 12. Sheath 30 has a length about equal to the length of the portion 25 plus the scaffold/balloon length so that when end 30a abuts end 24 the sheath 30 will properly cover the entire scaffold/balloon 10/12 length.

Figure 1A:
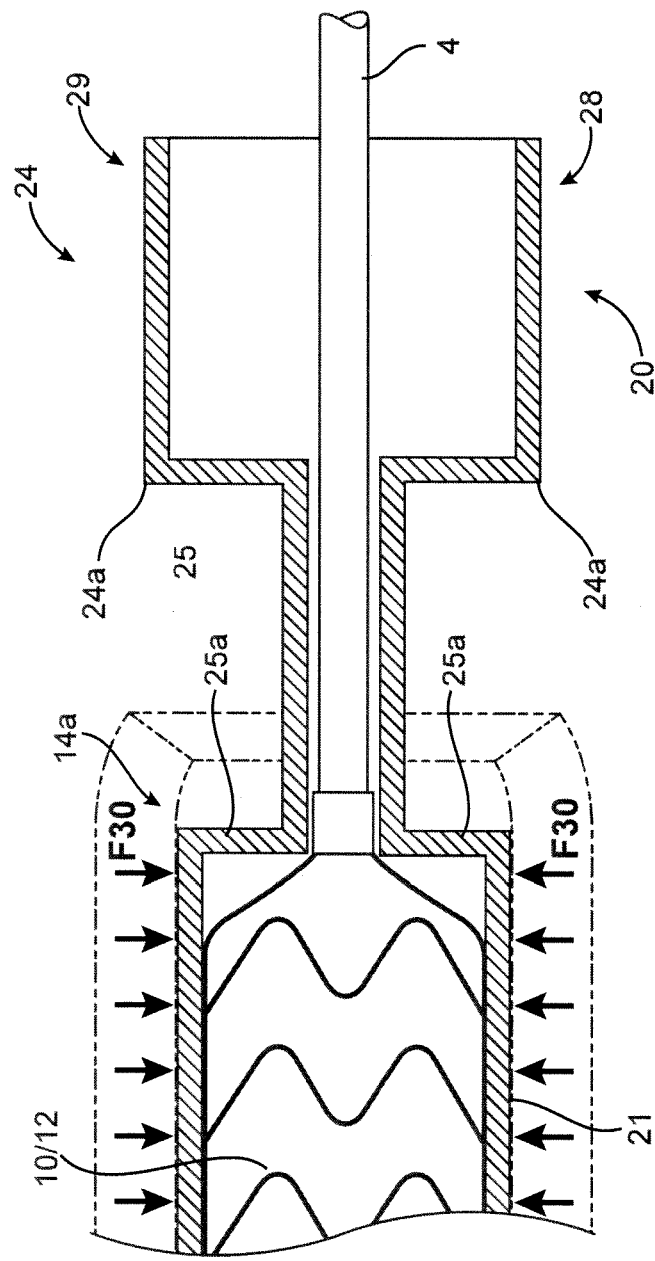
FIG. 1A shows a side view cross-section of a portion of the device of FIG. 1 at a proximal end thereof.

Portion 25 discourages removal of the sheath 20 prior to removal of sheath 30 from the scaffold 10. FIG. 1A shows the distal end 20a with the sheath 30 (shown in phantom) replaced by the inwardly directed preload F30 it applies to sheath portion 21 when positioned over the scaffold 10. A distal end of portion 25 forms a ledge 25a. When sheath 30 is positioned over the scaffold 10 the inwardly directed preload F30 applied to sheath portion 21 urges the halves 29, 28 together. With the halves 28, 29 urged together, the scaffold/balloon proximal end 14a blocks movement of the sheath 20 to the left in FIG. 1A by interfering with the movement of the ledge 25a to the left. Thus, if a user attempts to pull the sheath 20 off prior to removing the sheath 30 from the scaffold 10 area (which can damage the scaffold/balloon integrity), there will be resistance to this movement due to the ledges 25a abutting the balloon proximal end 14a (the ledge 25a thus may be thought of as an interference or interfering ledge part of the sheath 20). This resistance should indicate to the user that the sheaths 20, 30 are being removed in an improper manner. When the sheaths 20, 30 are removed properly, the first sheath 30 is moved to the distal end 20b of the sheath 20 (thereby removing the preload F30) so that the halves 28, 29 freely open up to allow the ledge 25a to easily pass over the scaffold 10 so that sheath 20 is removed without resistance. The user is thereby informed that the sheath 20 is removed properly when there is no resistance to removing the sheath 20 from the balloon-catheter assembly 2.

Thus, scaffold-balloon integrity is protected by the presence of the halves 28, 29 and the notched portion 25, as discussed above. The extended length of sheath 20, beyond the tip 6, e.g., is about equal to a length of the scaffold 10, the length of the sheath 30 or greater than both. This length beyond the distal end 6 facilitates an intuitive sliding removal or attachment of the sheath 30 from/to the scaffold 10 by respectively sliding the sheath 30 along the sheath 20 extension that is distal of tip 6 of the catheter assembly 2. The length of the sheath 20 that extends beyond the distal end 4 of the catheter assembly 2 (length L21 in FIG. 4A) may depend on the choice of sheaths used. For example, from the perspective of the health professional removal process, if the sheath 20 is more stiff (e.g., higher wall thickness and/or modulus) relative to the sheath 30 then the length beyond distal end 4 for sheath 20 may be longer so that the halves 28, 29 sheath 20 can be more safely displaced from the scaffold 10 by clearing the sheath 30 more distally of the scaffold 10. If the sheath 30 wall thickness and/or modulus is higher relative to sheath 20 than the length may be shorter since the sheath 30 will tend to naturally open up the halves 28, 29 as it is moved distally of the tip 6. Also, a thicker or higher modulus sheath 20 and/or sheath 30 may be desirable to increase the resistance to improper removal of sheath 20, e.g., as when a user attempts to remove sheath 20 with, or before removing sheath 30 from the scaffold 10 (as discussed earlier).

Figure 2A:
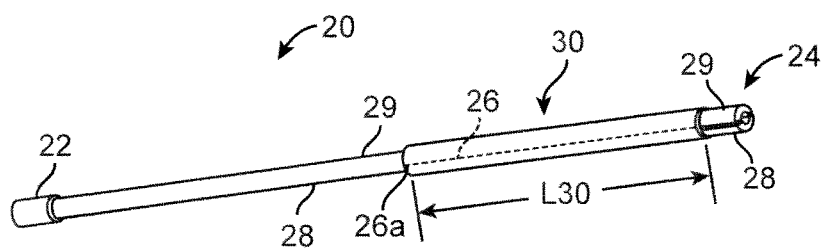
FIG. 2A is a perspective view of the sheath pair of FIG. 1.
Figure 2B:
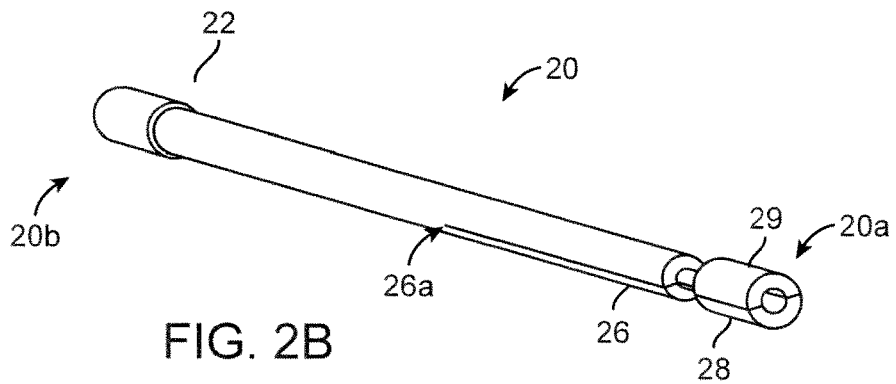
FIGS. 2B-2D show a side view, and first and perspective views of a protecting sheath of the sheath pair of FIG. 2A.
Figure 2C:
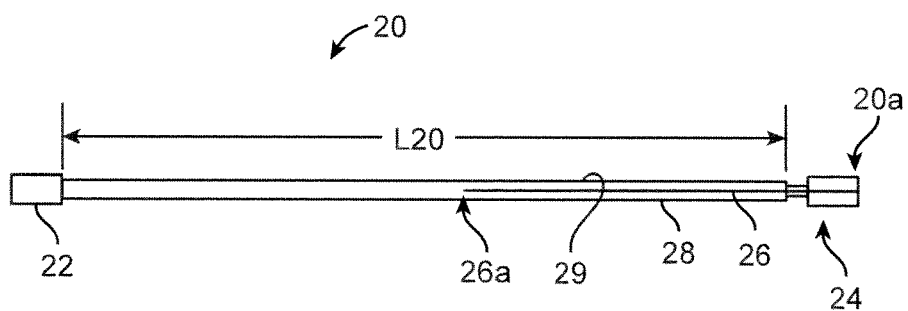
Figure 2D:
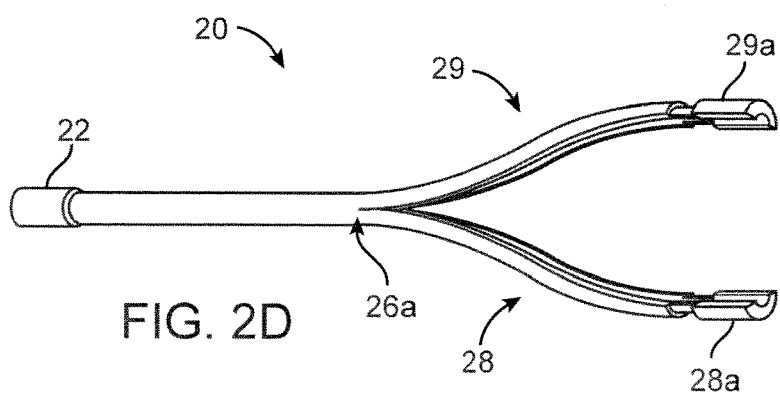

Referring to FIGS. 2B-2D, there are shown various views of the sheath 20. FIG. 2A shows the sheath 20 with the sheath 30. As mentioned above sheath 30 is sized to have a length L30 such that sheath 30 applies a sufficiently uniform radial inward force or preload on the scaffold 10 when end 30a abuts end 24a. The length L30 should therefore be slightly greater than the length of the scaffold-balloon structure. The sheath 30 can be slid towards or away from the scaffold location (i.e., its location in FIG. 2A or FIG. 1) over the sheath outer surface 20. As noted earlier, the sheath 20 has separable upper and lower halves 29, 28 formed by a cut 26 made across the tube forming sheath 20. FIG. 2D is a perspective view of the upper and lower halves 28, 29 separated from each other. As can be appreciated from this view, the halves 28, 29 rotate about the hinge 26a when they separate. FIGS. 2B and 2C show an additional side and perspective view, respectively, of the sheath 20 showing the aforementioned structure, including the portions of notched or stepped portion 25 and end 24 discussed earlier.

The length L20 in FIG. 2C should be chosen to extend over the scaffold 10 length as well as a sufficient distance beyond the scaffold 10 so that the sheath 30 can be pushed onto the scaffold 10, and removed from the scaffold 10 while the halves 28, 29 are disposed over the scaffold 10. The length L20 may be at least twice the length of sheath 30, i.e., L20=2*L30, to achieve this purpose. This length should be sufficient to allow the upper and lower halves 28, 29 to peel or rotate about the living hinge 26a and freely away from the scaffold surface (as in FIG. 2D) without interference from the sheath 30.

As mentioned earlier, a thicker tube and smaller inner diameter for sheath 30 will cause the sheath 30 to apply a greater pre-load on the scaffold 10. The sheath 30 thickness and/or inner diameter size is selected with the sheath 20 in mind. That is, the sizing of one can determine what sizing to use for the other, based on achieving an appropriate balance among the amount of pre-load F30 (FIG. 1A) desired, the ease in which the sheath 30 can be placed over or removed from the scaffold 10 location, increasing resistance to improper removal of sheath 20 (ledge 25a abutting proximal end 14a, as discussed above) and avoiding disruption to the integrity of the scaffold-balloon structure, e.g., pulling the scaffold 10 off the balloon when the sheath 30 is being removed. For example, if a relatively thin and/or low modulus tube is used for sheath 20 (as compared to sheath 30), the sheath 30 will impose a higher localized pre-load on the scaffold 10. And the scaffold 10 is more likely to be affected by sheath 30 movement because the sheath 20 easily deforms under the movement of the sheath 30. If the sheath 20 is made thick and/or a higher modulus tube material is used for sheath 20 (compared to sheath 30) the scaffold 10 will not be as affected by movement of the sheath 30. And local changes in pre-load on the scaffold 10 will tend to be lower since the sheath 20 does not deform as easily under the movement of the sheath 30.

Referring to FIGS. 3A-3D, methods of assembly using the sheaths 20, 30 (sheath pair) are now described. The scaffold 10 is crimped to the balloon 12 of the catheter assembly 2 using a crimping mechanism. As noted above, for a polymer scaffold the diameter reduction during crimping may be 2:1, 2.5:1, 3:1, 4:1 or higher. This diameter reduction introduces high stresses in the scaffold structure. The memory in the material following crimping causes recoil of the scaffold structure, as discussed earlier.

One can incorporate lengthy dwell times within the crimper, e.g., after the final crimp step, to allow stress-relaxation to occur in the structure while heated crimper blades are maintaining a fixed diameter and temperature to facilitate stress relaxation. Both the dwell period and the disposing of a constraining sheath over the crimped scaffold after crimping helps to reduce recoil after crimping. Crimping of the scaffold 10 to the balloon 12 including desirable dwell times and temperatures that can affect stress relaxation and recoil after crimping are disclosed in U.S. Publication Nos. US20120261858, US20120042501 and US20120285609.

Figure 3A:
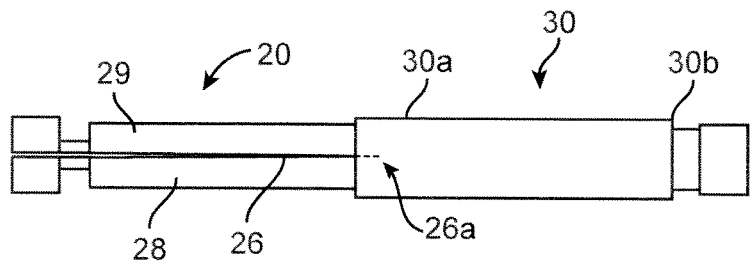
FIGS. 3A-3D illustrate a method of securing the sheath pair of FIG. 2A to a distal end of the catheter assembly of FIG. 1.

The sheath pair, shown in FIG. 3A, is placed on a mandrel 8 before being attached to the catheter assembly 2. The mandrel 8 is passed through the catheter shaft 4 guidewire lumen (not shown), and exits at the distal end 6 of the catheter assembly 2. The sheath pair is then placed on the mandrel 8 distally of the catheter assembly 2. The mandrel 8 is then used to guide the sheath pair over the scaffold-balloon 10/12 as illustrated in FIGS. 3B-3D.

Figure 3B:
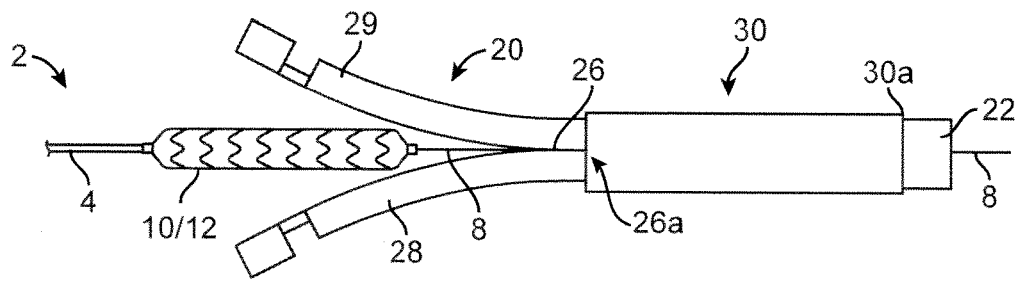

Referring to FIG. 3B, the distal end 30a of the sheath 30 is adjacent to the raised end 22 of the sheath 20. In this configuration the halves 28, 29 can freely open or close. The sheath pair is then brought towards the scaffold-balloon 10/12. The halves 28, 29 easily deflect over the scaffold-balloon 10/12. The sheath pair may be slid towards the scaffold-balloon 10/12 as follows. Holding the catheter assembly 2 stationary, grasping the mandrel 8 with one hand and the sheath pair with the other hand and sliding the sheath pair over the mandrel 8 until the halves 28, 29 are located over the scaffold-balloon 10/12 as shown in FIG. 3C. When properly positioned, the portions 24, 25 are positioned with respect to proximal end 14a as shown in FIG. 1A.

Figure 3C:
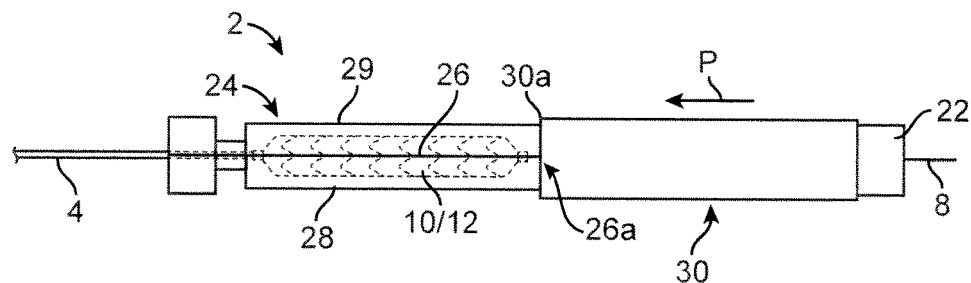
Figure 3D:
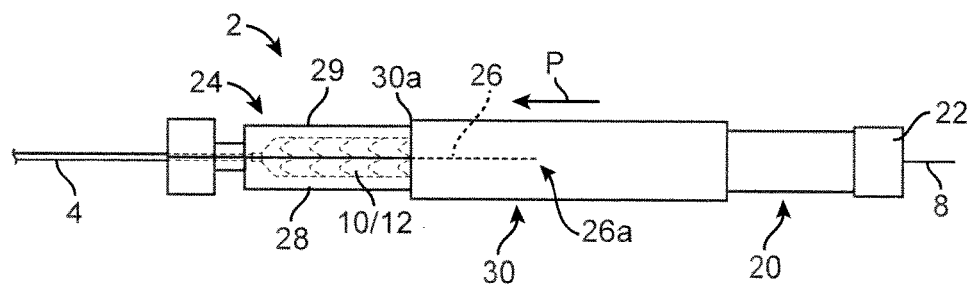

Referring to FIGS. 3C-3D, once the halves 28, 29 are located properly over the scaffold-balloon 10/12 to protect this structure, the constraining sheath 30 can be pushed over the scaffold-balloon 10/12 (as indicated in FIGS. 3C-3D by P). The sheath 30 may be pushed over the scaffold-balloon 10/12 in the following manner. The raised end 22 and mandrel 8 are grasped with one hand to hold the two stationary. Then, using the other hand the sheath 30 is pushed over the scaffold-balloon 10/12 until the end 30a of sheath 30 is disposed adjacent to, or abuts the raised end 24 of the sheath 20, which indicates the proximate location of the proximal end 14a of the balloon-scaffold 10/12. Alternatively, the portion 24 and catheter shaft 4 may be simultaneously held with on hand, while the sheath 30 is pushed towards the scaffold 10 with the other hand. By grasping the portion 24 with the catheter shaft 4, the halves 28, 29 are held in place relative to the scaffold 10 while the sheath 30 is being pushed over the scaffold 10.

Figure 4A:
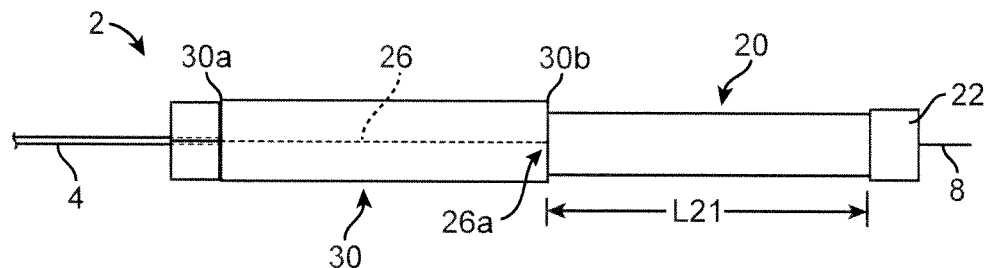
FIGS. 4A-4C illustrate a method of removing the sheath pair of FIG. 2A from the distal end of the catheter assembly of FIG. 1.

The catheter assembly 2 with sheaths arranged as in FIG. 4A is packaged and sterilized. At the time when the catheter assembly is to be used in a medical procedure the package is opened and the sheath pair removed from the distal end. The catheter assembly 2 is not configured for being introduced into the patient until the sheath pair is removed. FIGS. 1, 1A and 4A depict the arrangement of the sheaths 20, 30 at the distal end of the catheter assembly 2 when the packaged and sterile medical device is received by a health professional. Examples of such sterile packaging is found in U.S. patent publication no. US 2008-0010947. The sheath 20 extends well-beyond the distal end 6 of the catheter 2 assembly such that it overhangs the distal end 6. The overhanging portion of the sheath 20, which has a length of more than L21 (FIG. 4A), is provided to facilitate a safe and intuitive removal of the sheath pair by a health professional, thereby reducing the chances that the sheath pair are removed improperly.

Figure 4B:
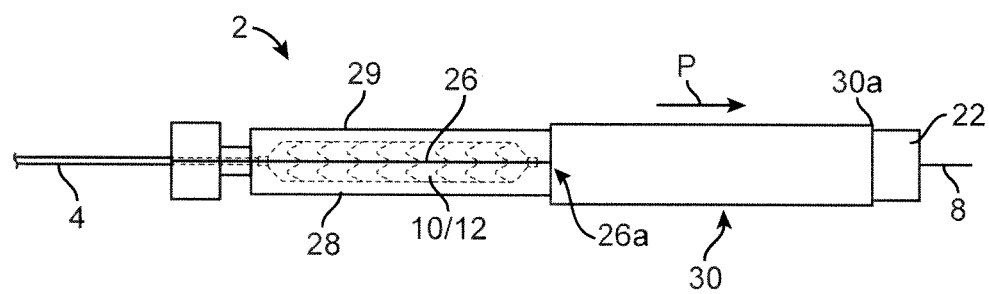
Figure 4C:
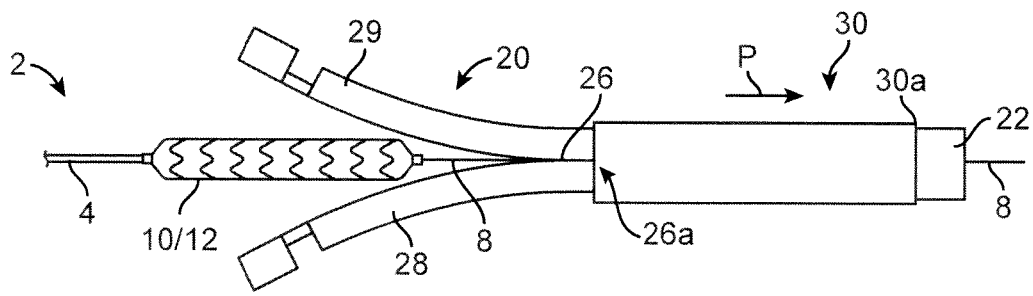

Referring to FIGS. 4B-4C, methods for removing the sheath pair from the scaffold-balloon 10/12 by the health professional are now described. These illustrations refer to moving the sheath pair over the mandrel 8; however, a mandrel 8 is not necessary. The sheath pair may be safely removed from the catheter assembly 2 without using a mandrel 8.

A sterilized and packaged catheter assembly with sheaths 20, 30 positioned as shown in 4A typically includes the stiffening mandrel 8 in the catheter shaft 4 lumen to provide bending stiffness for shaft 4. A distal end of the mandrel 8 has a curled end, or an extension/stop at the distal end (not shown), which is used to manually withdraw the mandrel 8 from the catheter shaft 4 lumen by pulling the mandrel 8 towards the distal end 6 of the catheter assembly 2. In the following example the sheaths 20, 30 are removed. The proscribed steps preferably also include the act of removing the mandrel 8 from the catheter shaft lumen by, e.g., simultaneously gripping the raised end 22, sheath 30 and mandrel 8.

First, the sheath 30 is pulled away from the scaffold-balloon 10/12 structure, where it is shown positioned in FIG. 4A. The sheath 30 may be withdrawn or pulled away from the scaffold-balloon 10/12 in the following manner. One hand grasps the raised end 22 and mandrel 8, to hold the two stationary, while the other hand grasps and pulls the sheath 30 towards the raised end 22. When the sheath 30 reaches the raised end 22 the halves 28, 29 should freely deflect away from the scaffold 10 surface, since a majority if not all of the cut 26 is to the left of the sheath 30 (FIG. 4B). At this point both sheaths 20, 30 can be simultaneously pulled away from the scaffold-balloon 10/12.

As an alternative, the sheaths 20, 30 may be removed by grasping the catheter assembly distal portion, e.g., the catheter shaft 4, and optionally portion 24 as well with one hand and grasping and pulling the sheath 30 distally of the catheter assembly 2 with the other hand. Once the sheath 30 has abutted the raised end 22 (and removing hand from portion 24, if being gripped with shaft 4), continued pulling on the sheath 30 distally can safely remove both sheaths without risk of dislodging the scaffold 10 from the balloon. The pulling of the sheath 30 distally, while it abuts the raised end 22, causes both the sheath 20 and the sheath 30 to be removed from the scaffold-balloon 10/12. The raised end 22 therefore functions as an abutment for removing both sheaths in a safe manner with minimal disruption to the crimped scaffold. This final pulling away of the sheath 20 from scaffold 10 may also simultaneously remove the stiffening mandrel 8 from the catheter shaft 4 lumen.

As discussed earlier, the assembly of sheaths 20, 30 discourages a health professional from removing the sheath 20 before sheath 30 is moved to end 22. For example, if a health professional were to pull on the end 22 while the sheath 30 is positioned over the scaffold, the ledges 25a abutting proximal end 14a will interfere with distal movement of the sheath (FIG. 1A). When this resistance is felt, this should indicate to the health professional that the sheath 20 is being removed in an improper manner. If the sheath 30 is first moved to end 22, then the sheath 20 can be pulled off of the catheter distal end 6 very easily since the halves 29, 28 (free of the preload F30) will easily open up and pass over the scaffold 10.

Figure 5A:
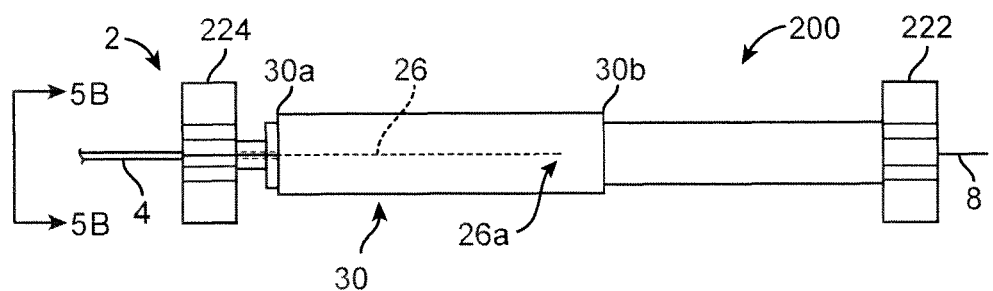
FIGS. 5A-5B illustrate side and front views of an alternative embodiment of a protecting sheath.
Figure 5B:
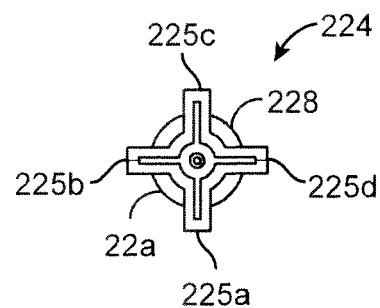

Referring to FIGS. 5A-5B there is illustrated an alternative embodiment of the sheath 20, which will be referred to as sheath 200. This sheath has raised abutments or surfaces 224, 222 formed at the distal and proximal ends of sheath 200. Otherwise the sheath 200 has the same construction as sheath 20. The raised end 224 forms proximal ends of halves 228, 229. And the sheath 200 has the cut 226 and hinge point 226a.

The proximal abutment 224 is shown in a frontal view in FIG. 5B. In this view the abutment 224 may take the form of a cross having ends 225a, 225b, 225c and 225d. The ends 225 form raised abutment surfaces that prevent or resist the sheath 30 from being moved to the left of the sheath 200 when the two are positioned over the scaffold. For example, when the packaged catheter assembly is being transported to a medical facility, the sheath 30 may slip proximally of the scaffold 10, thereby removing the constraint on the scaffold. By placing the abutment 225 at the proximal end of the sheath 200, the sheath 30 cannot move proximally. The same type of abutment 222 may also be formed at the distal end.

In a method of assembly the raised ends 222, 224 may be formed after the sheaths 20, 30 have been positioned over the scaffold-balloon 10/12 structure using, e.g., a hand crimper. The hand crimper is applied at the location 224 to form the cross members 225 (FIG. 5B) and also at the distal end of sheath 200 a similar structure 222.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for assembling a scaffold-balloon catheter, comprising:
    using a balloon-catheter including a balloon;
    using a scaffold comprising a polymer having a glass transition temperature (TG);
    using a crimping mechanism, crimping the scaffold to the balloon, the crimping including raising the temperature of the scaffold to between TG and 15 degrees Celsius below TG and maintaining the scaffold at a fixed diameter for a dwell period within the crimping device to reduce recoil of the scaffold; and
    after the dwell period, removing the scaffold from the crimping mechanism and constraining the scaffold including placing a protecting sheath over the scaffold to protect the scaffold, then placing a constraining sheath over the protecting sheath and the scaffold to constrain recoil in the scaffold;
    wherein the scaffold is configured for being passed through the body of a patient only after the constraining sheath and protecting sheath are removed from the scaffold.

2. The method of claim 1, wherein the placing the protecting sheath over the scaffold includes pushing the protecting sheath towards the scaffold until a proximal end of the protecting sheath is placed at a proximal end of the scaffold.

3. The method of claim 2, wherein the protecting sheath is on a mandrel and located distally of the scaffold when the protecting sheath is pushed towards the scaffold.

4. The method of claim 2, wherein the protecting sheath has separable halves, and wherein the halves open when the protecting sheath is pushed towards the scaffold.

5. The method of claim 1, wherein the placing the constraining sheath over the protecting sheath and the scaffold includes the constraining sheath being pushed onto a cut portion of the protecting sheath.

6. The method of claim 1, wherein the crimping includes a plurality of dwell periods.

7. The method of claim 1, wherein the constraining sheath has a higher wall thickness than the protecting sheath, and/or a material used for the constraining sheath has a higher modulus than a material used for the protecting sheath.

8. The method of claim 1, wherein the crimping mechanism comprises blades and the blades are set at a final crimped diameter for the dwell period, and wherein a ratio of a starting or pre-crimp diameter to the final crimped diameter is 2.5:1, 3:1 or higher.

9. A method for assembling a scaffold-balloon catheter, comprising:
    using a balloon-catheter including a balloon and a scaffold comprising a polymer having a glass transition temperature (TG);
    crimping the scaffold to the balloon using an iris crimping mechanism having a crimp head, the crimping including:
    raising the temperature of the scaffold to a temperature between TG and 15 degrees Celsius below TG, and
    crimping the scaffold to the balloon including reducing a diameter of the scaffold from a first diameter to a second diameter; and
    maintaining the crimp head at a final crimp head diameter for a dwell period to reduce recoil in the scaffold; and
    after the dwell period, removing the scaffold from the iris crimping mechanism and constraining the scaffold including placing a constraining and protecting sheath over the scaffold to protect and reduce recoil of the scaffold, wherein the sheath extends past a distal end of the scaffold by a length at least equal to a length of the scaffold;
    wherein the scaffold is configured for being passed through the body of a patient only after the sheath is removed from the scaffold.

* * * * *